United States Patent [19]
DeVries et al.

[11] Patent Number: 5,567,835
[45] Date of Patent: Oct. 22, 1996

[54] PREPARATION OF A VINYLSILOXANE-BENZOCYLOBUTENE FROM A HYDROLYZABLE VINYLSILANE-BENZOCYLOBUTENE

[75] Inventors: Robert A. DeVries; Edmund J. Stark, both of Midland, Mich.

[73] Assignee: The Dow Chemical Company, Midland, Mich.

[21] Appl. No.: 549,136

[22] Filed: Oct. 27, 1995

[51] Int. Cl.$^6$ ............................................. C07F 7/08
[52] U.S. Cl. ............................................. 556/453
[58] Field of Search ............................................. 556/453

[56] References Cited

U.S. PATENT DOCUMENTS

| | | |
|---|---|---|
| 4,642,329 | 2/1987 | Kirchhoff et al. . |
| 4,724,260 | 2/1988 | Kirchhoff et al. . |
| 4,812,588 | 3/1989 | Schrock . |
| 4,822,930 | 4/1989 | Liu . |
| 5,136,069 | 8/1992 | DeVries et al. . |
| 5,138,081 | 8/1992 | DeVries et al. . |
| 5,243,068 | 9/1993 | DeVries et al. . |
| 5,416,233 | 5/1995 | DeVries et al. ............ 556/453 X |
| 5,491,250 | 2/1996 | Stark et al. ............ 556/453 X |

OTHER PUBLICATIONS

Bower, Kenneth E. et al., *Polymer Bulletin 27*, pp. 129–133 (1991).
DeVries et al., *12th North American Catalyst Society Meeting*, May 5–9 (1991).
Harrod et al., *Organic Synthesis via Metal Carbonyls*, pp. 673–704 (1977).
Lewis, Larry N. et al., *Organometallics*, vol. 10, pp. 3750–3759 (1991).
Merker, Robert L. et al., *J. Am. Chem. Soc.*, vol. 81, pp. 975–978 (1959).
Plueddemann, Edwin P., *Silane Coupling Agents*, pp. 32–33 and 49–73 (1982).
Speier, John L. et al., *Advances In Organometallic Chemistry*, vol. 17, pp. 407–447 (1979).

*Primary Examiner*—Paul F. Shaver
*Attorney, Agent, or Firm*—Reid S. Willis

[57] ABSTRACT

This invention relates to a novel process for preparing vinylsiloxane-BCBs (vinylsiloxane-benzocyclobutenes) comprising reacting a hydrolyzable hydrosilating reagent with an acetylene-BCB in the presence of a catalyst, then hydrolyzing the hydrolyzable vinylsilane-BCB to form a vinylsiloxane-BCB.

9 Claims, No Drawings

PREPARATION OF A VINYLSILOXANE-BENZOCYLOBUTENE FROM A HYDROLYZABLE VINYLSILANE-BENZOCYLOBUTENE

BACKGROUND OF THE INVENTION

This invention relates to a novel process for preparing a vinylsiloxane-benzocyclobutene, the polymers of which are useful for the preparation of multichip modules and integrated circuits.

Schrock (U.S. Pat. No. 4,812,588) describes a preparation of DVS-bisBCB (divinyltetramethyldisiloxane-bisbenzocyclobutene) involving the reaction between 4-BrBCB (3-bromobicyclo[4.2.0]octa-1,3,5-triene) and DVS-(1,3-divinyl-1,1,3,3-tetramethyldisiloxane) in the presence of a palladium catalyst.

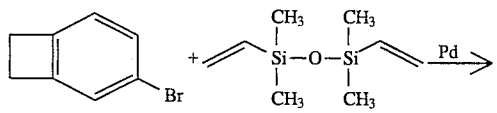

Schrock reported the product of this reaction to be represented by the following structure:

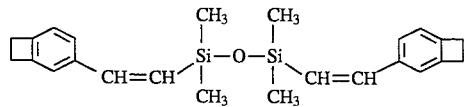

After Schrock's discovery, DeVries et al. (see 12th North American Catalyst Society Meeting, May 5–9, 1991, incorporated herein by reference) reported that the product of the reaction of 4-BrBCB and DVS under the Schrock conditions was, in fact, a mixture of isomers, predominantly the trans, trans isomer, with the trans,gem isomer being the most significant minor product:

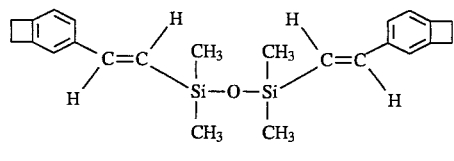

trans, trans-DVS-bisBCB (major product)

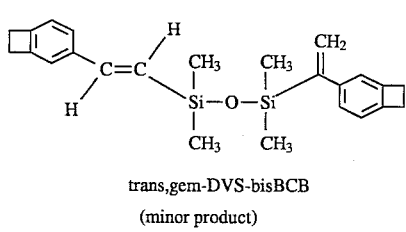

trans,gem-DVS-bisBCB (minor product)

One disadvantage of the Schrock method is that the DVS is of limited availability. A second disadvantage is that about 15 to 25% of the products of this reaction are side products. One of these side products, trans-ethylenebisbenzocyclobutene (trans-3,3'-(1,2-ethenediyl)bis[bicyclo(4.2.0)octa-1,3,5-triene]), is formed at percent levels (see U.S. Pat. Nos. 5,243,068 and 5,136,069, incorporated herein by reference) and may sporadically crystallize out of the product mixture, thereby causing both inconsistent product and problematic processing.

Still another disadvantage of the Schrock method is that the products of the method may require treatment with peroxides and extensive purification to remove unacceptably high quantities of phosphorous, bromine, and palladium. (See DeVries et al., U.S. Pat. No. 5,138,081, incorporated herein by reference.)

In view of the deficiencies of the art, it is desirable to find a synthetic route that can produce higher yields of desired vinylsiloxane-BCB products, that uses more readily available materials, and that requires less workup.

SUMMARY OF THE INVENTION

The present invention is a process comprising reacting a hydrolyzable hydrosilating reagent with an acetylene-BCB under such conditions to form a hydrolyzable vinylsilane-BCB, then hydrolyzing the hydrolyzable vinylsilane-BCB to form a vinylsiloxane-BCB.

A further aspect of the present invention is a process comprising:

a) reacting diphenylsilane, diethylsilane, or dimethylsilane, or a mixture thereof with an acetylene-BCB under such conditions to form an incompletely hydrosilated vinylsilane-BCB, then b) hydrolyzing the incompletely hydrosilated vinylsilane-BCB to form a divinyldisiloxane-bisBCB.

The present invention addresses a need in the art by making a useful product in higher yields and from more readily available starting materials than those described in the art, and by a process requiring less workup than known heretofore.

Detailed Description of the Invention

In the present invention, a hydrolyzable hydrosilating reagent is reacted with an acetylene-BCB (ethynylbicyclo [4.2.0]octa-1,3,5-triene) under such conditions to form a hydrolyzable vinylsilane-BCB. The hydrolyzable vinylsilane-BCB is then hydrolyzed to form a vinylsiloxane-BCB.

The acetylene-BCB may be 3-acetylene-BCB (2-ethynylbicyclo[4.2.0]octa-1,3,5-triene), 4-acetylene-BCB (3-ethynylbicyclo[4.2.0]octa-1,3,5-triene), an inertly substituted 3-acetylene-BCB, or an inertly substituted 4-acetylene-BCB. Any substituents that do not interfere with hydrosilation and do not poison the catalyst are acceptable. The preferred acetylene-BCBs are 3-acetylene-BCB and 4-acetylene-BCB; the more preferred acetylene-BCB is 4-acetylene-BCB.

4-Acetylene-BCB can be prepared as described by Bower and Farona (see Polymer Bulletin 27, 129–133 (1991), herein incorporated by reference), wherein 4-BrBCB (3-bromobicyclo-[4.2.0]octa-1,3,5-triene) is reacted with trimethylsilylacetylene and catalytic amounts of bistriphenylphosphine palladium (II) chloride, triphenylphosphine, and cuprous iodide in the presence of a suitable solvent, such as triethylamine, to form the 1-trimethylsilyl-2-(4-benzocyclobutyl)acetylene intermediate. This intermediate is advantageously purified, preferably by distillation, to remove unreacted 4-BrBCB, then desilated with a methanolic solution of potassium carbonate to form 4-acetylene-BCB. (See also Kirchhoff et al., U.S. Pat. No. 4,724,260, column 16, incorporated herein by reference.)

The 4-BrBCB can be prepared in accordance with Liu (see U.S. Pat. No. 4,822,930, herein incorporated by reference). If 4-BrBCB is prepared in this manner, some 3-BrBCB (2-bromobicyclo-[4.2.0]octa-1,3,5-triene) may be formed as a side product. Generally, this off-isomer is not separated from the 4-BrBCB. Consequently, low percent levels of 3-acetylene-BCB are formed in the process of preparing 4-acetylene-BCB.

3-acetylene-BCB and 4-acetylene-BCB are defined by the following structures.

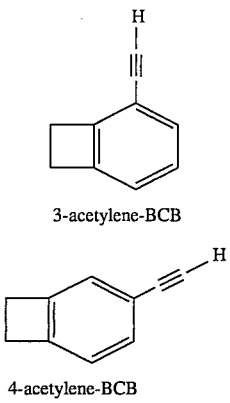

3-acetylene-BCB 4-acetylene-BCB

The term hydrosilation refers to an addition reaction in which a compound with one or more Si—H bonds adds to the acetylene group of the acetylene-BCB. Such compounds are referred to as hydrosilating reagents.

The hydrosilating reagents used in the process of the present invention have at least one Si—H bond, more preferably, one or two Si—H bonds, still more preferably not more than one Si—H bond per silicon atom, and can be linear, branched, cyclic, or polymeric. A hydrolyzable hydrosilating reagent also includes at least one functional group that is susceptible to removal by the addition of water. Preferred hydrolyzable hydrosilating reagents include silanes, halosilanes, and alkoxysilanes, or mixtures thereof. Chlorosilanes are more preferred.

In the following discussions, the prefix alkyl is used to refer to linear, branched, cyclic, or fluorinated aliphatic groups. The term aryl refers to aromatic, heteroaromatic, or inertly substituted aromatic or heteroaromatic groups.

Preferred silanes include dialkylsilanes, diarylsilanes, and arylalkylsilanes. More preferred silanes are dialkylsilanes, such as dimethylsilane and diethylsilane; diarylsilanes, such as diphenylsilane; and arylalkylsilanes, such as ethylphenylsilane and methylphenylsilane.

Preferred chlorosilanes include polychlorosilanes, such as trichlorosilane and dichloroalkylsilanes; and monochlorosilanes including chlorodialkylsilanes, chlorodiarylsilanes, and chloroarylalkylsilanes; with monochlorosilanes being more preferred. The preferred monochlorosilanes are chlorodialkylsilanes, such as chlorodimethylsilane and chlorodiethylsilane; and chlorodiarylsilanes, such as chlorodiphenylsilane. The most preferred monochlorosilane is chlorodimethylsilane.

Preferred alkoxysilanes include trialkoxy-silanes, alkyldialkoxysilanes, dialkylalkoxysilanes, dialkoxysilanes, and alkylalkoxysilanes; with dialkylalkoxysilanes being more preferred. The preferred dialkylalkoxysilanes are dialkylethoxysilanes, with diethylethoxysilane and dimethylethoxysilane being more preferred.

The most preferred hydrolyzable hydrosilating reagent is chlorodimethylsilane.

The hydrolyzable hydrosilating reagent is preferably reacted with a sufficient amount of an acetylene-BCB to convert at least one of the Si—H moieties per molecule of the hydrolyzable hydrosilating reagent to a hydrolyzable vinylsilane-BCB moiety. A vinylsilane-BCB is characterized by a C=C group bonded a) to an aromatic carbon of the BCB moiety; and b) to a silicon atom. The silicon atom may be geminal, cis, or trans to the BCB moiety. A hydrolyzable vinylsilane-BCB may be represented structurally as shown:

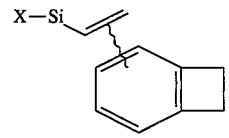

wherein X is represents a hydrolyzable functional group, preferably chloro, alkoxy, or H, more preferably chloro; the squiggly line represents a bond between the 3- or 4-position of the BCB moiety, and either carbon atom of the Si—C=C group.

Hydrosilation is carried out in the presence of a hydrosilation-promoting catalyst. Examples of hydrosilation-promoting catalysts include nickel, palladium, rhodium, cobalt, iron, iridium, platinum, or complexes thereof; or benzoyl peroxide. (See Harrod and Chalk, "Hydrosilation Catalyzed by Group VIII Complexes" in Wender and Pino, *Organic Syntheses via Metal Carbonyls*, pp. 673–704 (1977), incorporated herein by reference). Of these, a complex of platinum is preferred, particularly platinum on carbon, $Pt_2(DVS)_3$ (see Lewis et al., *Organometallics*, Vol. 10, p. 3750 (1991), incorporated herein by reference), or chloroplatinic acid hexahydrate, (see J. L. Speier, "Homogeneous Catalysis of Hydrosilation by Transition Metals," *Adv. Organomet. Chem.*, Vol. 17, p 407 (1979), incorporated herein by reference). The more preferred catalyst is chloroplatinic acid hexahydrate.

When the catalyst is a platinum complex, it is convenient to dissolve the catalyst in an unreactive solvent, then add an aliquot of the solution to the reaction mixture. The aliquot preferably comprises about 0.01 to about 1 weight percent, more preferably about 0.05 to about 0.5 weight percent of the reaction mixture, based on the weight of the reactants. Suitable solvents include, but are not restricted to alcohols, such as ethanol, isopropanol, and butanol; glycols, such as ethylene glycol and propylene glycol; and inertly substituted aromatic, such as toluene and xylene. A preferred solvent for the platinum catalyst is isopropanol.

The hydrosilation reaction is advantageously carried out at a temperature sufficiently high to promote the reaction rate, yet sufficiently low to avoid polymerization. Because the reaction is exothermic, it may be desirable to control the rate of reaction by carrying out the reaction in the presence of sufficient quantities of a sufficiently high boiling solvent, which neither reacts with the reagent nor poisons the catalyst, and to provide a reflux temperature of the reaction mixture, preferably in the range of from about 50° C., more preferably in the range of about 80° C., to about 150° C., more preferably to about 125° C. Toluene is an example of a preferred solvent. The mixture is advantageously heated to a temperature suitable to initiate the exotherm, then maintained at a desired temperature, preferably the reflux temperature of the reaction.

The hydrosilation reaction may also be carried out in the absence of an exotherm-controlling solvent. For example, the acetylene-BCB can be added to a mixture of the hydrolyzable hydrosilating reagent and the catalyst at a rate sufficient to control the temperature and the rate of the reaction. In this mode of addition, the reaction temperature is maintained in the desired range, preferably by an external means of controlling temperature.

Where the hydrolyzable hydrosilating reagent is a halosilane or an alkoxysilane, this reagent is preferably reacted with the acetylene-BCB at about an equimolar ratio.

Where the hydrosilating reagent is a silane that does not contain chloro or alkoxy groups, it may be desirable to add an amount of acetylene-BCB that is insufficient to convert all of the Si—H moieties to vinylsilane-BCB moieties. A product of this insufficient addition of acetylene-BCB to a hydrosilating reagent is a vinylsilane-BCB that contains a hydrolyzable Si—H moiety, preferably a dialkyl-, diaryl-, or arylalkylvinylsilane-BCB, or a mixture thereof. This product of insufficient addition of acetylene-BCB may be hydrolyzed (as described in the following paragraph) to form useful products.

The hydrolyzable vinylsilane-BCB can be hydrolyzed to form a coupled product that forms presumably through a silanol intermediate.

A hydrolysable vinylsilane-BCB that contains an Si—Cl group can be reacted with water, preferably ice, and more preferably poured into an excess of ice, to form a coupled product, preferably a divinyldisiloxane-bisBCB. The coupled product can be isolated, for example, by extraction with a suitable solvent, such as toluene. The solvent can be removed in vacuo and the product can be optionally purified, preferably by distillation.

A hydrolyzable vinylsilane-BCB that contains an Si—H group can be hydrolyzed in the presence of water, an alcohol, and a catalytic amount of base. The preferred alcohol is ethanol and preferred bases are sodium hydroxide and potassium hydroxide, with potassium hydroxide being more preferred. A discussion of the hydrolysis of compounds containing Si—H groups can be found in R. L. Merker et al., *J. Am. Chem. Soc.*, Vol. 81, p. 975 (1959), incorporated herein by reference.

A hydrolyzable vinylsilane-BCB that contains an Si-alkoxy group can be hydrolyzed in the presence of catalytic amounts of acid or base. See Pludemann, *Silane Coupling Agents*, pp. 32–33 and 49–73 (1982), incorporated herein by reference.

The preferred hydrolyzable vinylsilane-BCBs include monochlorovinylsilane-BCBs, monoalkoxyvinylsilane-BCBs, dialkylvinylsilane-BCBs, diarylvinylsilane-BCBs, and arylalkylvinylsilane-BCBs, or mixtures thereof. Preferred monochlorovinylsilane-BCBs are chlorodialkylvinylsilane-BCBs such as chlorodimethylvinylsilane-BCB and chlorodiethylvinylsilane-BCB; chlorodiarylvinylsilane-BCBs such as chlorodiphenylvinylsilane-BCB; chloroarylalkylvinylsilane-BCBs such as chloroethylphenylvinylsilane-BCB, and chloromethylphenylvinylsilane-BCB.

Preferred monoalkoxyvinylsilane-BCBs include dialkylalkoxyvinylsilane-BCBs, with dialkylethoxyvinylisilane-BCBs, such as diethylethoxyvinylsilane-BCB and dimethylethoxyvinylsilane-BCB being more preferred.

Preferred dialkylvinylsilane-BCBs include dimethylvinylsilane-BCB and diethylvinylsilane-BCB; preferred diarylvinylsilane-BCBs include diphenylvinylsilane-BCB; and preferred arylalkylvinylsilane-BCBs include methylphenylvinylsilane-BCB and ethylphenyl-vinylsilane-BCB.

The more preferred hydrolyzable vinylsilaneBCBs are chlorodimethylvinylsilane-BCB, chlorodiethylvinylsilane-BCB, dimethylvinylsilane-BCB, and diethylvinylsilane-BCB. The most preferred hydrolyzable vinylsilane-BCB is chlorodimethylvinylsilane-BCB.

Thus, a hydrolyzable vinylsilane-BCB, preferably a chlorovinylsilane-BCB, more preferably a chlorodialkylvinylsilane-BCB, most preferably a chlorodimethylvinylsilane-BCB, is advantageously poured over an excess of ice to form a polyalkyl-, polyaryl-, or polyalkylpolyarylpolyvinylsiloxane-poly-BCB, preferably a dialkyldiaryl-, tetraalkyl- or tetraaryldivinyldisiloxane-bisBCB, more preferably 1,1,3,3-tetramethyldivinyldisiloxane-bisBCB, 1,1,3,3-tetraphenyldivinyldisiloxane-bisBCB, or 1,1,3,3-tetraethyldivinyldisiloxane-bisBCB; most preferably an isomeric mixture of DVS-bisBCBs, wherein the trans,trans-isomer is the major product; and wherein the product of hydrolysis contains preferably less than 1 weight percent, more preferably less than 0.5 weight percent, and most preferably less than 0.1 weight percent trans-ethylenebisbenzocyclobutene based on the weight of the vinylsilane-BCB.

Mixtures of different hydrolyzable vinylsilane-BCBs can be hydrolyzed to form a variety of coupled products. For example a mixture of chlorodimethylvinylsilane-BCB and chlorodiphenylvinylsilane-BCB can be poured over an excess of ice to form a mixture of products that includes 1,1,3,3-tetramethyldivinyldisiloxane-bisBCB, 1,1,3,3-tetraphenyldivinyldisiloxane-bisBCB, and 1,1-dimethyl-3,3-diphenyldivinyldisiloxane-bisBCB.

Because the amount of catalyst used in the reaction is so low, and because bromine-, and phosphorous-containing impurities are substantially removed in previous process steps, product workup is simplified. For example, a divinyldisiloxane-BCB suitable for subsequent B-staging may be obtained by passing the product over silica gel. If desired, an even purer divinyldisiloxane-BCB may be obtained by means such as distillation, preferably in vacuo distillation.

The vinylsiloxane-BCB formed by the hydrolysis of a hydrolyzable vinylsilane-BCB can be fully cured or partially cured (B-staged) in accordance with the procedures described in U.S. Pat. No. 4,642,329, herein incorporated by reference.

Example 1 - DVS-bisBCB from
Chlorodimethylsilane and 4-Acetylene-BCB

A tared 250-mL thermowell round-bottom flask equipped with a nitrogen-topped condenser, a magnetic stirrer, and a thermocouple-controlled heating mantle is charged with chlorodimethylsilane (49.1 g, 509 mmoles, 1.05 equivalents), 4-acetylene-BCB (66.9 g, 484moles, 1.00 equivalents), toluene (10 mL), and chloroplatinic acid hexahydrate (48 μL of a 10.0 mM solution in isopropanol, 0.48 μmoles, $10^{-6}$ equivalents) The mixture is flushed with nitrogen, stirred, and gently warmed at 50° C. under nitrogen for 3 hours, and reaction is monitored for an exotherm after an expected induction period. Capillary GC reveals slow conversion, so more catalyst (a total of $3.0 \times 10^{-6}$ equivalents) is added. The temperature is slowly brought to 90° C. as the decreasing reflux rate allows. The reaction is cooled to room temperature and poured over ice water, monitoring for completion of the hydrolysis by capillary GC. The mixture is extracted with methylene chloride, and the aqueous phase back-extracted with methylene chloride (25 mL). The combined organics are washed with water, dried over $MgSO_4$, filtered, concentrated by rotary evaporation, and further concentrated at 110° C. and 0.5 torr. The concentrate has an isomer ratio of 85.8% trans,trans-, and 9.1% trans,gem-DVS-bisBCB, and 5.1% of an unidentified isomer. The DVS-bisBCB isomers comprise 84.1% of the crude product (excluding solvent), the rest being largely mono-adducts and unreacted 4-acetylene-BCB. This concentrate is distilled in a short-path wiped-film still at 160° C. and $2 \times 10^{-3}$ torr, affording 80.8 g of pale overheads (86% yield). The impurity trans-ethylenebisbenzocyclobutene was not detected by gas chromatography above 0.1% by weight, based on the weight of the DVS-bisBCB isomers.

What is claimed is:

1. A process comprising reacting a hydrolyzable hydrosilating reagent with an acetylene-BCB under such conditions to form a hydrolyzable vinylsilane-BCB, then hydrolyzing the hydrolyzable vinylsilane-BCB to form a vinylsiloxane-BCB.

2. The process of claim 1 which is carried out in the presence of a platinum catalyst.

3. The process of claim 2 wherein the platinum catalyst is chloroplatinic acid hexahydrate.

4. The process of claim 1 wherein the hydrolyzable silane is a chlorosilane.

5. The process of claim 4 wherein the acetylene-BCB is 4-acetylene-BCB and the chlorosilane is chlorodiphenylsilane, chloromethylphenylsilane, chlorodiethylsilane, chlorodimethylsilane, or a mixture thereof.

6. A process for preparing 1,1,3,3-tetramethyldivinyldisiloxane-bisBCB comprising the steps of:

a) reacting chlorodimethylsilane with 4-acetylene-BCB in the presence of chloroplatinic acid hexahydrate to form chlorodimethylvinylsilane-BCB, then b) hydrolyzing the chlorodimethylvinylsilane-BCB to form 1,1,3,3-tetramethyldivinyldisiloxane-bisBCB.

7. A process comprising the steps:

a) reacting diphenylsilane, diethylsilane, or dimethylsilane, or a mixture thereof with an acetylene-BCB under such conditions to form an incompletely hydrosilated vinylsilane-BCB, then b) hydrolyzing the incompletely hydrosilated vinylsilane-BCB to form a divinyldisiloxane-bisBCB.

8. The process of claim 7 wherein the reaction is carried out in the presence of chloroplatinic acid hexahydrate.

9. The process of claim 7 wherein the ratio of the acetylene-BCB to the diphenylsilane, diethylsilane, dimethylsilane, or a mixture thereof is about 1:1.

* * * * *